United States Patent [19]

Levitt

[11] 4,238,621

[45] Dec. 9, 1980

[54] INTERMEDIATES FOR HERBICIDAL SULFONAMIDES

[75] Inventor: George Levitt, Wilmington, Del.

[73] Assignee: E. I. Du Pont de Nemours and Company, Wilmington, Del.

[21] Appl. No.: 49,149

[22] Filed: Jun. 18, 1979

Related U.S. Application Data

[63] Continuation-in-part of Ser. No. 029,281, Apr. 13, 1979.

[51] Int. Cl.$^3$ .................................... C07C 143/828
[52] U.S. Cl. .................................... 560/12; 71/92; 71/93; 260/397.7 R; 260/465 D; 544/211; 544/321; 544/332; 560/13

[58] Field of Search ................ 260/465 D; 560/12, 13

[56] References Cited

U.S. PATENT DOCUMENTS

| | | | |
|---|---|---|---|
| 2,946,815 | 7/1960 | Hamor | 560/12 |
| 3,371,114 | 2/1968 | Sayigh et al. | 260/545 R |
| 3,379,758 | 4/1968 | Ulrich et al. | 260/545 R |
| 3,484,466 | 12/1969 | Sayigh et al. | 260/397.7 |

*Primary Examiner*—Dolph H. Torrence

[57] ABSTRACT

This invention relates to novel o-carbonylbenzenesulfonyl isocyanates and their use as intermediates for the preparation of sulfonylureas which are known to be active herbicides.

20 Claims, No Drawings

INTERMEDIATES FOR HERBICIDAL SULFONAMIDES

RELATED APPLICATIONS

This application is a continuation-in-part of my co-pending application U.S. Ser. No. 029,281 filed Apr. 13, 1979.

BACKGROUND OF THE INVENTION

U.S. Pat. No. 3,484,466 teaches a process in which an aromatic sulfonamide is phosgenated in the presence of an inert solvent and a catalytic amount of a hydrocarbyl isocyanate to form the corresponding arylsulfonyl isocyanate. 4-Carbethoxybenzenesulfonyl isocyanate is listed as a compound which can be prepared by this method.

In U.S. Pat. No. 3,379,758 arylsulfonyl monoisocyanates and arylsulfonyl diisocyanates are produced by a process which comprises mixing in the range 0° to 175° C., phosgene and an arylsulfonylurea of the formula $Ar(SO_2NHCONHR)_n$, wherein n is one or two, R is alkyl of one to 8 carbon atoms, inclusive, and Ar is phenyl or phenylene, unsubstituted or substituted with one or two substituents selected from the class consisting of alkyl of one to 8 carbon atoms, inclusive, cycloalkyl of 3 to 8 carbon atoms, inclusive, phenyl, naphthyl, aralkyl of 7 to 10 carbon atoms, inclusive, alkoxy of one to 8 carbon atoms, inclusive, halogen, nitro, cyano, sulfo, amino, dialkylamino of 2 to 12 carbon atoms, inclusive, and alkoxycarbonyl of 2 to 8 carbon atoms, inclusive.

In U.S. Pat. No. 3,371,114 there is taught a process of converting an aromatic sulfonamide to the corresponding aromatic sulfonyl isocyanates. Phosgenation of the sulfonamide in the presence of a catalytic quantity of a hydrocarbyl isocyanate gives the desired sulfonyl isocyanate.

SUMMARY OF THE INVENTION

None of the above references teach the intermediates necessary to make an improved class of highly active herbicidal sulfonylureas taught in U.S. Ser. No. 029,281. According to the instant invention, such an intermediate has been discovered. The intermediate has the general formula

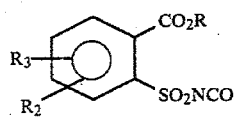   I wherein
R is $C_1$–$C_{12}$ alkyl; $C_3$–$C_{10}$ alkenyl; $C_2$–$C_6$ alkyl substituted with one to four substituents selected from 0–3 atoms of F, Cl, Br or 0–2 methoxy groups; $C_3$–$C_6$ alkenyl substituted with 1–3 atoms of F, Cl or Br; $C_5$–$C_8$ cycloalkyl; $C_5$–$C_8$ cycloalkenyl; $C_5$–$C_6$ cycloalkyl substituted with substituents selected from one to four methyl groups, methoxy, alkyl substituents of $C_2$–$C_4$, F, Cl or Br; $C_4$–$C_{10}$ cycloalkylalkyl; $C_4$–$C_8$ cycloalkylalkyl with 1–2 $CH_3$; —$CH_2CH_2OR_7$; $CH_2CH_2CH_2OR_7$ or

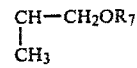

where $R_7$ is —$CH_2CH_3$, $CH(CH_3)_2$, phenyl, —$CH_2CH_2Cl$, —$CH_2CCl_3$; —$(CH_2CH_2O)_{\overline{n}}R_8$ or

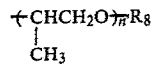

where $R_8$ is $CH_3$, —$CH_2CH_3$ —$CH(CH_3)_2$, phenyl, —$CH_2CH_2Cl$ or —$CH_2CCl_3$, and n' is 2 or 3
$R_2$ is H, Cl, Br, F, $C_1$–$C_3$ alkyl, —$NO_2$, —$OCH_3$, —$SCH_3$, $CF_3$, $SO_2CH_3$, $N(CH_3)_2$ or CN; and
$R_3$ is H, Cl, Br or $CH_3$.

Preferred are the following:

2. A compound of the generic scope where the carbon of R bonded to O is also bonded to at least one H.

3. A compound of the preferred (2) where $R_3$ is H and is para to the sulfonyl group.

4. A compound of preferred (3) where R is $C_1$–$C_6$ alkyl, $C_3$–$C_6$ alkenyl, $C_2$–$C_4$ alkyl substituted with one to four substituents selected from 0–3 F, Cl, 0–2 $OCH_3$ or $C_3$–$C_4$ alkenyl substituted with 1–3 Cl; $C_5$–$C_6$ cycloalkyl; $C_5$–$C_6$ cycloalkenyl; $C_5$–$C_6$ cycloalkyl substituted with up to four methyl groups, methoxy, $C_2H_5$ or chloro; $C_4$–$C_7$ cycloalkylalkyl; —$CH_2CH_2OR_7$,

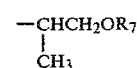

or —$CH_2CH_2CH_2OR_7$ where $R_7$ is as previously defined; —$(CH_2CH_2O)$–$_2R_8$ or

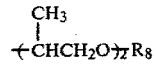

where $R_8$ is as previously defined.

5. Compounds of preferred (4) where $R_2$ is H, Cl, $CH_3$ or $NO_2$.

Compounds of preferred (5) where $R_2$ is H.

More preferred are:

6. Compounds of preferred (3) where R is $C_1$–$C_4$ alkyl, $C_3$–$C_4$ alkenyl; $C_2$–$C_3$ alkyl substituted with —$OCH_3$ or Cl; $C_3$ alkenyl substituted with 1–3 Cl; $C_5$–$C_6$ cycloalkyl; cyclohexenyl; cyclohexyl substituted with 1–3 —$CH_3$ or —$CH_2CH_2OR_7$ where $R_7$ is —$C_2H_5$, —$CH(CH_3)_2$, phenyl, —$CH_2CH_2Cl$; or

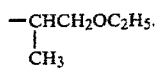

7. Compounds of preferred (6) where $R_2$ is as defined in preferred (5).

8. Compounds of preferred (6) where $R_2$ is H.

9. Compounds of preferred (3) where R is $C_1$–$C_4$ alkyl, $C_3$–$C_4$ alkenyl, $C_2$–$C_3$ alkyl substituted with Cl;

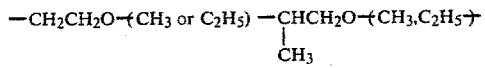

or —$CH_2CH_2CH_2O(CH_3$ or $C_2H_5)$.

10. Compounds of preferred (9) where $R_2$ is as defined in preferred (4).

11. Compounds of preferred (9) where $R_2$ is as defined in preferred (8).

The following species are particularly preferred.
o-Methoxycarbonylbenzenesulfonyl isocyanate;
o-Ethoxycarbonylbenzenesulfonyl isocyanate;
o-Isopropoxycarbonylbenzenesulfonyl isocyanate;
o-(2-Chloroethoxy)carbonylbenzenesulfonyl isocyanate;
o-Allyloxycarbonylbenzenesulfonyl isocyanate;
2-Methoxycarbonyl-5-nitrobenzenesulfonyl isocyanate;
2-Methoxycarbonyl-5-chlorobenzenesulfonyl isocyanate; and
2-Isopropoxycarbonyl-5-nitrobenzenesulfonyl isocyanate.

Synthesis

Herbicidal compounds of Formula III are prepared as shown in Equation 1 by the reaction of an appropriately substituted o-carbonylbenzenesulfonyl isocyanate of this invention with an appropriate aminopyrimidine or aminotriazine. Thus, o-carbonylbenzenesulfonyl isocyanates are important intermediates for the preparation of these herbicides.

Formula III

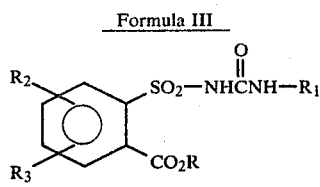

wherein

R, $R_2$ and $R_3$ are as described above and $R_1$ is

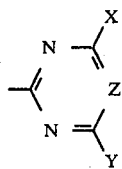

where X and Y are selected from $OCH_3$ or $CH_3$ and Z is

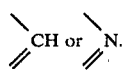

Equation 1

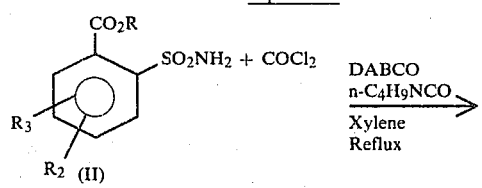

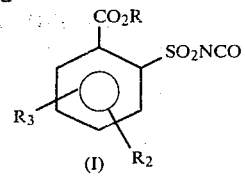

A mixture of the appropriate sulfonamide, e.g. an o-alkoxycarbonyl benzenesulfonamide II such as the methyl ester, which is known in the art, a hydrocarbyl isocyanate such as butyl isocyanate and a catalytic amount of a tertiary amine base such as 1,4-diaza[2,2,2]bicyclooctane (DABCO) in xylene or other inert solvent of sufficiently high boiling point (e.g. $> 135°$) is heated to approximately 135° C. Phosgene is added to the mixture until an excess of phosgene is present as indicated by a drop in the boiling point. The mixture is then heated further to drive off the excess phosgene. After the mixture is cooled and filtered to remove a small amount of insoluble by-products, the solvent and alkyl isocyanate are distilled off in-vacuo leaving a residue which is the crude sulfonyl isocyanate I.

The hydrocarbyl isocyanates which are useful in the process are also described in the above-cited patent, U.S. Pat. No. 3,371,114. As disclosed therein, the only limitation on the nature of the hydrocarbyl moiety is that it should be free from substituents which are reactive with phosgene. Preferred in this invention for reasons of efficiency and economy are the $C_4-C_{10}$ alkyl isocyanates and the $C_5-C_8$ cycloalkyl isocyanates. For the purposes of this invention, a catalytic quantity of hydrocarbyl isocyanate will generally consist of an amount equal to about 0.2 to 1.0 mole of hydrocarbyl isocyanate per mole of arylsulfonamide.

The phosgenation reaction is carried out in the presence of a catalytic quantity of a tertiary amine base. Any tertiary amine base free of substituents reactive with phosgene may be used. Classes of tertiary amines which could be used include, but are not limited to, aliphatic, cycloaliphatic, aliphaticaromatic, heterocyclic and aliphaticheterocyclic amines. Preferred for reasons of availability are those tertiary amines containing from three to ten carbon atoms and one to two nitrogen atoms. Examples of such bases are pyridine, triethylamine, 1,4-diazabicyclo[2,2,2]-octane, 4-dimethylaminopyridine, N,N-dimethylaniline, trimethylamine, N,N-diethylaniline, N-methylpiperidine, and N,N-dimethylpiperazine. Preferred for reasons of efficiency and economy are 1,4-diazabicyclo[2,2,2]-octane and triethylamine.

The tertiary amine base must be present in a catalytic quantity. This will generally be in the range of about 0.2 to 5.0 grams of base per mole of arylsulfonamide.

The process of this invention is generally carried out within a temperature range of about 100°–175° C. although temperature is not critical. Pressure is also not critical, and atmospheric pressure is typically used.

The time required for the reaction to go to substantial completion may be readily monitored by techniques familiar to one skilled in the art, e.g., titration of the effluent hydrogen chloride gas or infrared analysis of the reaction mixture. Typically, the reaction time will be in the range of about 1 to 24 hours.

A suspension of the appropriate arylsulfonamide II in an inert solvent, a catalytic quantity of hydrocarbyl isocyanate and a catalytic quantity of a tertiary amine base are heated, with stirring, to reflux. The solvent can be any inert solvent with a boiling point within the range of about 100°-200° C.; examples of suitable solvents are xylene, chlorobenzene, mesitylene, toluene, pentachloroethane and octane. Phosgene is then introduced under a refrigerated reflux condenser at such a rate that the temperature of the reaction mass is maintained at about 5° to 8° C. below the boiling point of the solvent. Following the phosgene addition, the reaction mixture is heated to drive off the small amount of excess phosgene, and is then cooled and filtered to remove small amounts of any by-product.

The filtered solution can be used directly to make compounds useful as herbicides. Alternatively, the product can be isolated by evaporation of the solvent and the hydrocarbyl isocyanate, leaving the high boiling arylsulfonyl isocyanate I as a residue. Generally, these arylsulfonyl isocyanates I can be distilled at reduced pressure or used without further purification.

In Equation 1 R, $R_2$ and $R_3$ are as defined above.

Intermediates of Formula II are prepared, for example, by the procedures of B. Loev and M. Kormendy, J. Org. Chem. 27, 1703-1709, 2177-2180, 2448-2452 (1962), which are herein incorporated by reference.

As shown in Equation 2, compounds of Formula III, wherein R, $R_2$ and $R_3$ are as defined for Equation 1, and $R_1$ is as defined for Formula III, are conveniently prepared by reacting an appropriately substituted carbonylbenzenesulfonyl isocyante of Formula I with an appropriately substituted aminopyrimidine or aminotriazine of Formula IV.

Equation 2

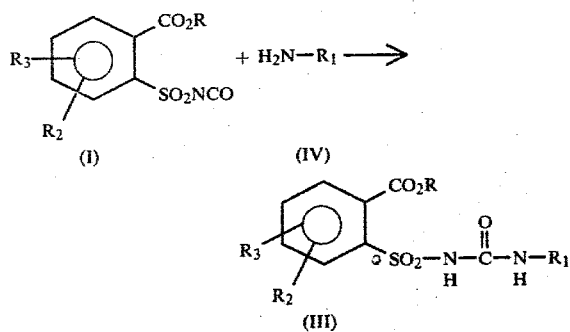

The reaction of Equation 2 is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of amine IV. Since such isocyanates are liquids, low melting solids or are readily soluble in solvents such as those listed above, their addition can be easily controlled.

The reaction is generally exothermic. In some cases, the desired product is soluble in the warm reaction medium and on cooling crystallizes in pure form. Other products which are soluble in the reaction medium are isolated by evaporation of the solvent, trituration of the solid residue with solvents such as 1-chlorobutane or ethyl ether, and filtration.

In the following Examples, all temperatures are in °C. and all parts are by weight unless otherwise indicated.

EXAMPLE 1

Methyl 2-(isocyanatosulfonyl)benzoate

A stirred mixture containing 157 g of methyl 2-sulfamoylbenzoate, 73 g of butyl isocyanate 0.3 g of 1,4-diazabicyclo[2,2,2]octane and 1.0 l of xylene was heated to reflux for one half hour. Phosgene gas was then passed into the system under a dry ice reflux condenser allowing the reaction temperature to drop to 120°. This addition was continued until the reflux temperature remained at 120° without further phosgene addition. The temperature of the reaction mixture was then raised to 136° (by removal of the dry ice reflux condenser) after which it was cooled to room temperature and filtered. Evaporation of the filtrate yielded the desired crude sulfonyl isocyanate which could be purified by distillation at 132°-138° C. under 1.0 to 1.1 mm of mercury pressure. The product is extremely reactive with water so contact with moisture should be scrupulously avoided.

EXAMPLE 2

Isopropyl 2-(isocyanatosulfonyl)benzoate

To 60.7 g (0.25 mole) of isopropyl 2-sulfamoylbenzoate in 300 ml dry (molecular sieves) xylenes was added 25.0 g (0.25 mole) n-butyl isocyanate and 0.1 n-1,4-diazabicyclo[2,2,2]octane. The mixture was heated to reflux temperature and phosgene was slowly bubbled through the solution for 2 hours.

An infrared spectrum of the reaction mixture indicated formation of the desired sulfonyl isocyanate (2250 $cm^{-1}$). The resulting cloudy solution was cooled to room temperature and decanted from a small amount of solid impurity. Evaporation of the resulting clear solution yielded the desired crude sulfonyl isocyanate, which was used in subsequent steps without further purification.

By using the procedures of Examples 1 and 2 with equivalent amounts of the appropriate sulfamoylbenzoate, alkyl isocyanate, 1,4-diazabicyclo[2,2,2]octane and phosgene, the compounds of Table I can be prepared. Infrared absorption peaks listed in Table I for the isocyanate and o-carbonyl groups are given in reciprocal centimeters ($cm^{-1}$).

TABLE I

| R | $R_2$ | $R_3$ | $cm^{-1}$ |
|---|---|---|---|
| $-CH_2CH_3$ | H | H | 2250,1725 |
| $-CH_2CH_2CH_3$ | H | H | |
| $-CH_2(CH_2)_2CH_3$ | H | H | 2250,1720 |
| $-CH_2(CH_2)_3CH_3$ | H | H | |
| $-CH_2(CH_2)_4CH_3$ | H | H | 2215,1720 |
| $-CH(CH_3)_2$ | H | H | 2225,1710 |
| $-CHCH_2CH_3$ <br> $\|$ <br> $CH_3$ | H | H | 2215,1705 |
| $-CH_2CH(CH_3)_2$ | H | H | |
| $-CH_2CH_2CH(CH_3)_2$ | H | H | 2250,1725 |
| $-\langle S \rangle$ | | | |
| $-CH_2(CH_2)_8CH_3$ | H | H | 2210,1710 |
| $-CH_2CH_2Cl$ | H | H | 2200,1710 |
| $-CH_2CH_2OCH_2CH_3$ | H | H | |
| $-CH_2CH_2OCH_2CH_2Cl$ | H | H | |

TABLE I-continued

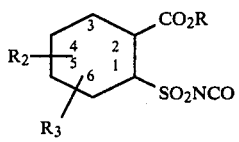

| R | R2 | R3 | cm⁻¹ |
|---|---|---|---|
| —(CH₂CH₂O)₂CH₂CH₂Cl | H | H | 2230,1730 |
| —CH₂CH₂O—Ph | H | H | 2250,1730 |
| —CH₂CH=CH₂ | H | H | 2250,1725 |
| —CH₃ | 4-Cl | H | 2200,1715 |
| —CH₃ | 4-F | H | 2220,1725 |
| —CH₃ | 4-Cl | 5-Cl | |
| —CH₃ | 5-Cl | H | 2210 |
| —CH₃ | 5-NO₂ | | |
| n-C₁₂H₂₅ | H | H | |
| —(cyclo)C₈H₁₅ | 5-OCH₃ | H | |
| —CH₂CH=CH—CH₂Cl | 4-Cl | 5-CH₃ | |
| —CH₂—(cyclo)C₆H₁₁ | 4-CH₃ | H | |
|  | 5-SO₂CH₃ | H | |
| —CH₂—cyclohexyl-CH₃ | | | |
| —CH₂—CCl₃ | 5-CF₃ | H | |
| —CH₃ | 5-N(CH₃)₂ | H | |
| —CH₃ | 5-CN | H | |
| —CH₃ | 5-SCH₃ | H | |
| —CH₃ | 5-Br | H | |
| —CH(CH₃)₂ | 5-NO₂ | H | |
| —CH₂—CH=CH—CH₂Cl | H | H | |
| —CH(CH₂Cl)—CH=CH₂ | H | H | |
| —CH₂—CH₂—C(Cl)=CHCl | H | H | |
| —CH₂—CH=CH—CH(F)—Cl | H | H | |
| —CH₂—CCl=CCl₂ | H | H | |
| cyclohexenyl | H | H | |
| cyclooctenyl | H | H | |
| cyclopentyl-CH₃ | H | H | |
| 2,2,3-trimethylcyclopentyl | H | H | |
| 2,2,4,4-tetramethylcyclohexyl | H | H | |
| cyclohexyl-OCH₃ | H | H | |
| 2-methoxycyclohexyl | H | H | |
| cyclohexyl-C(CH₃)₃ | H | H | |
| —CH₂—CH=CH—(CH₂)₅CH₃ | H | H | |
| —CH₂(CH₂)₇—CH=CH₂ | H | H | |
| (CH₂)₄—CH=CH—CH₃ | H | H | |
| (CH₂)₅CH₂Cl | H | H | |

TABLE I-continued

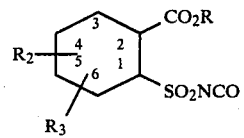

| R | R2 | R3 | cm⁻¹ |
|---|---|---|---|
| —CH(CH₃)—CH₂Cl | H | H | |
| —(CH₂)₅CCl₃ | H | H | |
| —CH₂CBr₃ | H | H | |
| —CH₂CF₃ | H | H | |
| —CH₂—CHCl—CHClCH₃ | H | H | |
| —(CH₂)₂—OCH₃ | H | H | |
| —(CH₂)₃—OCH₃ | H | H | |
| (CH₂)₆OCH₃ | H | H | |
| —CH₂—CH(OCH₃)—CH₂—OCH₃ | H | H | |
| —CH₂—C(Cl)=CH₂ | H | H | |
| CH₂CH₂CH₂O—CH(CH₃)₂ | H | H | |
| CH(CH₃)—CH₂OC₂H₅ | H | H | |
| —CH(CH₃)—CH₂O—Ph | H | H | |
| —CH₂CH₂OCH₂CCl₃ | H | H | |
| (CH₂CH₂O)₇CH₃ | H | H | |
| (CH₂CH₂O)₇CH(CH₃)₂ | H | H | |
| (CH₂CH₂O)₂—Ph | H | H | |
| (CH(CH₃)CH₂O)₂CH₂CCl₃ | H | H | |
| (CH₂CH₂O)₃CH₂CH₂Cl | H | H | |
| (CH(CH₃)—CH₂O)₃CH₂CH₃ | H | H | |
| ethylcyclohexyl | H | H | |
| chlorocyclohexyl | H | H | |
| fluorocyclohexyl | H | H | |
| bromocyclohexyl | H | H | |
| —CH₂-cyclopropyl | H | H | |
| —CH₂-cyclopentyl | H | H | |
| —CH₂CH₂—cyclo-C₈H₁₅ | H | H | |
| —CH₂-(dimethylcyclohexyl) | H | H | |
| —CH₂-(dimethylcyclopentyl) | H | H | |

EXAMPLE 3

N-[(4,6-Dimethylpyrimidin-2-yl)aminocarbonyl]-2-methoxycarbonylbenzenesulfonamide To 37 g of 2-amino-4,6-dimethylpyrimidine in 500 ml of anhydrous acetonitrile was added 67 g of 2-methoxycarbonylbenzenesulfonyl isocyanate with stirring at ambient temperature. The resulting mixture was thereafter stirred for sixteen hours and then filtered to remove the desired product which had precipitated as a white solid, m.p. 198°–202°. It showed infrared absorption peaks at 1750, 1700, 1600 and 1550 cm$^{-1}$, consistent for the desired compound.

EXAMPLE 4

N-[(Pyrimidine-2-yl)aminocarbonyl]-2-methoxycarbonylbenzenesulfonamide

With stirring at ambient temperature, 1.0 g of 2-aminopyrimidine in 25 ml of anhydrous acetonitrile was added to 2.4 g of 2-methoxycarbonylbenzenesulfonyl isocyanate. After stirring that mixture for 24 hours, the resultant precipitate was filtered off to yield 2.2 g of the desired compound which melted at 188°–192°. Its showing infrared absorption peaks at 1700, 1680 and 1580 cm$^{-1}$ is consistent for N-[(pyrimidin-2-yl)aminocarbonyl]-2-methoxycarbonylbenzenesulfonamide.

EXAMPLE 5

N-[(4-Methoxy-6-methylpyrimidin-2-yl)aminocarbonyl]-2-methoxycarbonylbenzenesulfonamide To a stirred suspension of 1.4 g of 2-amino-4-methoxy-6-methylpyrimidine in 30 ml of anhydrous methylene chloride was added at ambient temperature 2.4 g of 2-methoxycarbonylbenzenesulfonyl isocyanate. After stirring for 16 hours, the foregoing mixture was filtered to remove unreacted amine, and the filtrate evaporated at temperatures up to 40° and reduced pressure. The resultant residue was stirred in 25 ml of water, the pH adjusted to 10 by the addition of 50% sodium hydroxide and the solution filtered. Acidification of the filtrate to pH 3 with hydrochloric acid caused precipitation of the desired product which was removed by filtration and dried to yield 0.8 g of product melting at 173°–179°. It showed infrared absorption peaks at 1720, 1680, 1630 and 1550 cm$^{-1}$, consistent for N-[(4-methoxy-6-methylpyrimidin-2-yl)aminocarbonyl]-2-methoxycarbonylbenzenesulfonamide.

EXAMPLE 6

N-[(4,6-Dimethoxypyrimidin-2yl)aminocarbonyl]-2-methoxycarbonylbenzenesulfonamide A mixture containing 1.6 g of 2-amino-4,6-dimethoxypyrimidine, 30 ml of anhydrous methylene chloride and 2.4 g of 2-methoxycarbonylbenzenesulfonyl isocyanate was stirred at ambient temperature and pressure for 16 hours. It was then filtered to remove unreacted amine and the filtrate evaporated at temperatures up to 40° and reduced pressure. The residue thus obtained was stirred in 25 ml of water, the pH adjusted to 10 by the addition of 50% aqueous sodium hydroxide and the solution filtered. Acidification of the filtrate to pH 3 caused the formation of a precipitate. Filtration and drying the precipitate yielded 1.7 g of the desired product, melting at 185°–190°. Its infrared absorption peaks at 1700 and 1710 cm$^{-1}$ are consistent for the desired structure and the nuclear magnetic resonance absorption peaks at 3.8 and 3.85 are consistent for the two different types of methoxy groups brought together in this product.

EXAMPLE 7

N-[(4,6-Dimethoxy-1,3,5-triazin-2-yl)aminocarbonyl]-2-(2-chloroethoxycarbonyl)benzenesulfonamide To 0.7 g of 2-amino-4,6-dimethoxy-1,3,5-triazine in 10 ml anhydrous methylene chloride solvent was added 1.45 g 2-($\beta$-chloroethoxycarbonyl)benzenesulfonyl isocyanate. After stirring at ambient temperature for sixteen hours the solvent was removed under reduced pressure, the residue triturated with ether and the solid product filtered off, yield 1.21 g, m.p. 171°–174° C. The solid showed infrared absorption peaks at 1705 and 1715 cm$^{-1}$, consistent for N-[(4,6-dimethoxy-1,3,5-triazin-2-yl)aminocarbonyl]-2-(2-chloroethoxycarbonyl)benzenesulfonamide.

EXAMPLE 8

N-[(4-Methoxy-6-methyl-1,3,5-triazin-2-yl)aminocarbonyl]-2-(2-chloroethoxycarbonyl)benzenesulfonamide To 0.7 g of 2-amino-4-methoxy-6-methyl-1,3,5-triazine in 10 ml anhydrous methylene chloride solvent was added 1.45 g 2-($\beta$-chloroethoxycarbonyl)benzenesulfonyl isocyanate with stirring at ambient temperature. The mixture was thereafter stirred for sixteen hours. The solvent was evaporated under reduced pressure and the residue triturated with hexane and filtered to yield 1.72 g of compound which melted at 167°–170° C. The solid showed infrared absorption peaks at 1700 and 1705 cm$^{-1}$, consistent for N-[(4-methoxy-6-methyl-1,3,5-triazin-2-yl)aminocarbonyl]-2-(2-chloroethoxycarbonyl)benzenesulfonamide.

EXAMPLE 9

N-[(4,6-Dimethoxy-1,3,5-triazine-2-yl)aminocarbonyl)]-2-(isopropoxycarbonyl)benzenesulfonamide To 0.7 g of 2-amino-4,6-dimethoxy-1,3,5-triazine suspended in 5.0 ml anhydrous methylene chloride was added 1.6 g of 2-isopropoxycarbonylbenzenesulfonyl isocyanate in 5.0 ml of anhydrous methylene chloride. The resulting mixture was filtered to remove some unreacted 2-amino-4,6-dimethoxytriazine, the methylene chloride filtrate was evaporated at reduced pressure and the residue triturated with chlorobutane to yield 0.5 g of desired product melting at 192°–195° C. The solid showed infrared absorption peaks at 1705 and 1715 cm$^{-1}$ consistent for N-[(4,6-dimethoxy-1,3,5-triazin-2-yl)aminocarbonyl]-2-(isopropoxycarbonyl)benzenesulfonamide.

EXAMPLE 10

N-[(4-Methoxy-6-methyl-1,3,5-triazine-2-yl)aminocarbonyl]-2-(isopropoxycarbonyl)benzenesulfonamide To 26.8 g of 2-amino-4-methoxy-6-methyl-1,3,5-triazine in 300 ml anhydrous methylene chloride was added 67.0 g of 2-isopropoxycarbonylbenzenesulfonyl isocyanate in 100 ml anhydrous methylene chloride. The resultant suspension was stirred at ambient temperature for 72 hours, and filtered to yield 40.0 g of the desired product as a white solid, m.p. 193°–196° C. The solid showed infrared absorption peaks at 1700 and 1710 cm$^{-1}$ consistent for N-[(4-methoxy-6-methyl-1,3,5-triazin-2-yl)aminocarbonyl]-2-(isopropoxycarbonyl)benzenesulfonamide.

EXAMPLE 11

N-[(4,6-Dimethoxy-1,3,5-triazin-2-yl)aminocarbonyl]-2-methoxycarbonylbenzenesulfonamide A mixture of 1.6 g of 2-amino-4,6-dimethoxy-1,3,5-triazine, 25 ml of anhydrous methylene chloride and 2.4 g of 2-methoxycarbonylbenzenesulfonyl isocyanate was stirred at ambient temperature for 16 hours. It was then filtered to remove unreacted amine and the filtrate evaporated at temperatures up to 40° under reduced pressure. The residue was triturated with butyl chloride and filtered to yield the desired compound which melted above 170° with decomposition.

EXAMPLE 12

N-[(4-Methoxy-6-methyl-1,3,5-triazin-2-yl)aminocarbonyl]-2- methoxycarbonylbenzenesulfonamide To an anhydrous suspension of 1.4 g of 2-amino-4-methoxy-6-methyl-1,3,5-triazine in 25 ml of methylene chloride was added with stirring at ambient temperature and pressure 2.4 g of 2-methoxycarbonylbenzenesulfonyl isocyanate. The mixture was thereafter stirred for 16 hours and filtered. The filtrate was evaporated to dryness, the residue was triturated with butyl chloride and the product removed by filtration. The product thus obtained melted at 165°, and had absorption peaks in the infrared at 1550, 1600, 1680 and 1700 cm$^{-1}$ and in the NMR spectrum at 2.5, 3.65, 4.0 with an aromatic multiplet at 7.2–8 ppm.

The activity of compounds of Formula III can be seen in greenhouse and field tests. The tests are described and the data resulting from them are shown below. The ratings are based on a numerical scale extending from 0=no effect, to 10=maximum effect. The accompanying descriptive symbols have the following meanings:

C=chlorosis or necrosis
D=defoliation
E=emergence inhibition
G=growth retardation
H=formative effects
U=unusual pigmentation
6Y=abscised buds or flowers

Test A

Seeds of crabgrass (Digitaria spp.), barnyardgrass (Echinochloa crusgalli), wild oats (Avena fatua), cassia (Cassia tora), morningglory (Ipomoea spp.), cocklebur (Xanthium ssp.), sorghum, corn, soybean, rice, wheat and nutsedge tubers (Cyperus rotundus) were planted in a growth medium and treated preemergence with a nonphytotoxic solvent solution of the compounds of Table II. Other batches of seeds and tubers for all of the foregoing weed and crop plants were planted at the same time as controls. The control plantings were untreated; i.e., neither any compound nor any solvent was applied. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three-five leaves were sprayed with a nonphytotoxic solvent solution of the compounds of Table II. Other groups of all the same weed and crop plants were sprayed with the same nonphytotoxic solvent so as to provide control plants. Preemergence and postemergence treated plants and controls were maintained in a greenhouse for sixteen days, then all treated plants were compared with their respective controls and rated visually for response to treatment. The data in Table II shows that the compounds of this invention are very effective as herbicides.

TABLE II

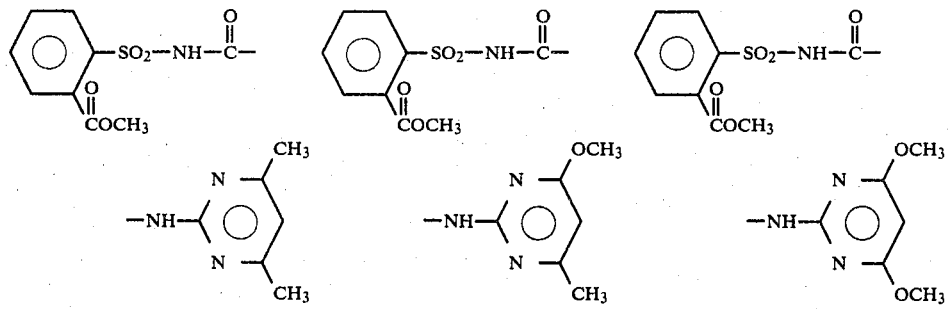

| kg/ha | 0.4 | 2.0 | 0.4 | 0.4 |
|---|---|---|---|---|
| POST-EMERGENCE | | | | |
| BUSHBEAN | 9C | 9C | 9C | 9C |
| COTTON | 9C | 9C | 9C | 9C |
| MORNINGGLORY | 10C | 10C | 10C | 10C |
| COCKLEBUR | 10C | 9C | 9C | 9C |
| CASSIA | 9C | 9C | 9C | 9C |
| NUTSEDGE | 9C | 9C | 9C | 10C |
| CRABGRASS | 9C | 9C | 5C,9G | 5C,8G |
| BARNYARDGRASS | 10C | 10C | 9C | 9C |
| WILD OATS | 9C | 9C | 9C | 9C |
| WHEAT | 9C | 9C | 9C | 9C |
| CORN | 9C | 9C | 10C | 9C |
| SOYBEAN | 9C | 6C,9G | 9C | 9C |
| RICE | 10C | 10C | 5C,9G | 8C |
| SORGHUM | 9C | 10C | 9C | 9C |
| PRE-EMERGENCE | | | | |
| MORNINGGLORY | 9G | 9G | 9G | 9G |

TABLE II-continued

| | | | | |
|---|---|---|---|---|
| COCKLEBUR | 9G | 9G | 9G | 9G |
| CASSIA | 8G | 9G | 9G | 9G |
| NUTSEDGE | 10E | 10E | 10E | 10E |
| CRABGRASS | 9G | 9G | 9H | 9H |
| BARNYARDGRASS | 9H | 9H | 9H | 9H |
| WILD OATS | 3C,9H | 3C,9H | 9H | 9H |
| WHEAT | 9H | 9H | 9H | 9H |
| CORN | 10E | 10E | 10H | 9H |
| SOYBEAN | 9H | 9H | 9H | 10E |
| RICE | 10E | 10E | 10E | 10E |
| SORGHUM | 10E | 10E | 9H | 9H |

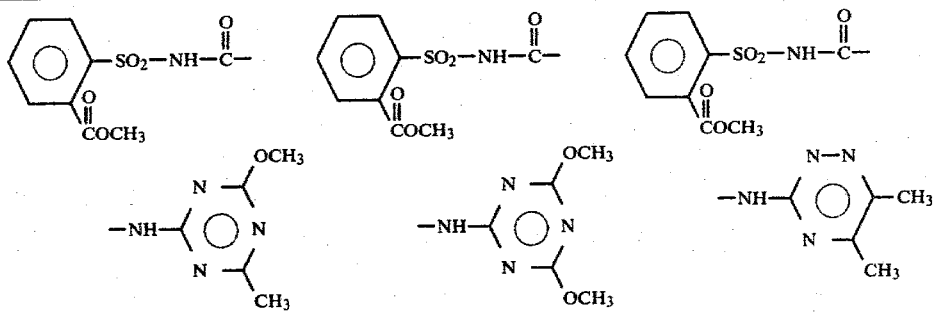

| kg/ha | 0.4 | 0.4 | 2 |
|---|---|---|---|
| POST-EMERGENCE | | | |
| BUSHBEAN | 9C | 9C | 5C,10D |
| COTTON | 9C | 5U,5C,9G | 5C,9G |
| MORNINGGLORY | 10C | 10C | 5C,9G |
| COCKLEBUR | 9C | 9C | 9C |
| CASSIA | — | 9C | 9C |
| NUTSEDGE | 9C | 9C | 9C |
| CRABGRASS | 10C | 9C | 9C |
| BARNYARDGRASS | 10C | 10C | 9C |
| WILD OATS | 10C | 4C,7G | 9C |
| WHEAT | 10C | 3C,7G | 10C |
| CORN | 10C | 10C | 5U,9C |
| SOYBEAN | 9C | 9C | 9C |
| RICE | 10C | 10C | 9C |
| SORGHUM | 10C | 9C | 9C |
| PRE-EMERGENCE | | | |
| MORNINGGLORY | 9H | 9G | 9C |
| COCKLEBUR | 9G | 9G | 9G |
| CASSIA | 9G | 9G | 9C |
| NUTSEDGE | 10E | 9G | 10E |
| CRABGRASS | 10E | 9H | 4C,9G |
| BARNYARDGRASS | 9H | 9H | 9H |
| WILD OATS | 9H | 9G | 9H |
| WHEAT | 9H | 9G | 9H |
| CORN | 10E | 9G | 9G |
| SOYBEAN | 9H | 9H | 9H |
| RICE | 10E | 10E | 10E |
| SORGHUM | 9H | 9G | 9H |

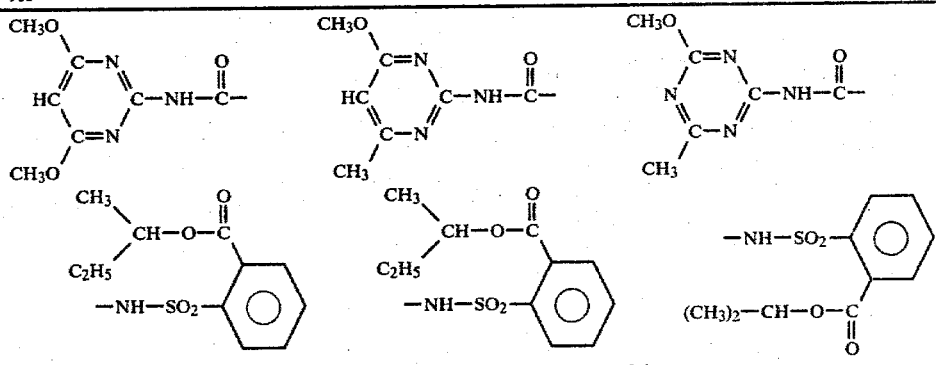

| kg/ha | 0.4 | 0.4 | 0.4 |
|---|---|---|---|
| POST-EMERGENCE | | | |
| BUSHBEAN | 9D,9G | 9D,9G | 9C |
| COTTON | 6C,9G | 7C,9G | 9C |
| MORNINGGLORY | 9C | 10C | 10C |
| COCKLEBUR | 6C,9G | 9C | 10C |
| CASSIA | 5C,8G | 5C,8G | 10C |
| NUTSEDGE | 7G | 8G | 10C |

TABLE II-continued

| | | | |
|---|---|---|---|
| CRABGRASS | 2A | 0 | 5C,8G |
| BARNYARDGRASS | 9C | 5C,9H | 6C,9H |
| WILD OATS | 2C | 8G | 2C,6G |
| WHEAT | 1C | 5C,8G | 2C |
| CORN | 9H | 5C,9H | 10C |
| SOYBEAN | 9C | 3C,9G | 5C,9G |
| RICE | 4C,8G | 5C,9G | 5C,8G |
| SORGHUM | 2C,9G | 3C,9G | 5C,9G |
| PRE-EMERGENCE | | | |
| MORNINGGLORY | 9G | 9G | 9G |
| COCKLEBUR | 9G | 10E | 9G |
| CASSIA | 8G | 9G | 6C,9G |
| NUTSEDGE | 10E | 10E | 10E |
| CRABGRASS | 0 | 6G | 2C,6G |
| BARNYARDGRASS | 9H | 9H | 2C,9H |
| WILD OATS | 8G | 2C,9H | 9G |
| WHEAT | 2G | 9G | 5G |
| CORN | 2C,8G | 2U,9H | 9G |
| SOYBEAN | 8H | 9H | 9H |
| RICE | 10E | 10E | 10E |
| SORGHUM | 9G | 9H | 2C,9G |

What is claimed is:

1. A compound having the formula:

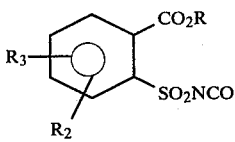

wherein

R is $C_1$-$C_{12}$ alkyl; $C_3$-$C_{10}$ alkenyl; $C_2$-$C_6$ alkyl substituted with one to four substituents selected from up to 3 atoms of F, Cl, Br, up to 2 methoxy groups; $C_3$-$C_6$ alkenyl substituted with 1-3 atoms of F, Cl, Br; $C_5$-$C_8$ cycloalkyl; $C_5$-$C_8$ cycloalkenyl; $C_5$-$C_6$ cycloalkyl substituted with substituents selected from up to four methyl groups, methoxy, alkyl substituents of $C_2$-$C_4$, F, Cl or Br; $C_4$-$C_{10}$ cycloalkylalkyl; or $C_4$-$C_8$ cycloalkylalkyl with 1-2 $CH_3$; $-CH_2CH_2OR_7$; $CH_2CH_2CH_2OR_7$ or

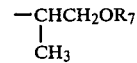

where $R_7$ is $-CH_2CH_3$, $CH(CH_3)_2$, phenyl, $-CH_2CH_2Cl$, $-CH_2CCl_3$; $-(CH_2CH_2O)_{n'}R_8$ or

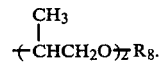

where $R_8$ is $CH_3$, $-CH_2CH_3$—$CH(CH_3)_2$, phenyl, $-CH_2CH_2Cl$ or $-CH_2CCl_3$, and $n'$ is 2 or 3;

$R_2$ is H, Cl, Br, F, $C_1$-$C_3$ alkyl, $-NO_2$, $-OCH_3$, $-SCH_3$, $CF_3$, $SO_2CH_3$, $N(CH_3)_2$ or $-CN$; and $R_3$ is H, Cl, Br or $CH_3$.

2. A compound of claim 1 where the carbon of R bonded to O is also bonded to at least one H.

3. A compound of claim 2 where $R_3$ is H and is para to the sulfonyl group.

4. A compound of claim 3 where R is $C_1$-$C_6$ alkyl, $C_3$-$C_6$ alkenyl, $C_2$-$C_4$ alkyl substituted with up to four substituents selected from up to 3 F or Cl and up to 2 $OCH_3$, $C_3$-$C_4$ alkenyl substituted with 1-3 Cl; $C_5$-$C_6$ cycloalkyl; $C_5$-$C_6$ cycloalkenyl; $C_5$-$C_6$ cycloalkyl substituted with up to four methyl groups, methoxy, $C_2H_5$ or chloro; $C_4$-$C_7$ cycloalkylalkyl; $-CH_2CH_2OR_7$,

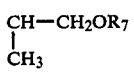

or $-CH_2CH_2CH_2OR_7$; $-(CH_2CH_2O)_2R_8$ or

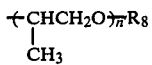

5. A compound of claim 4 where $R_2$ is H, Cl, $CH_3$ or $NO_2$.

6. A compound of claim 5 where $R_2$ is H.

7. A compound of claim 3 where R is $C_1$-$C_4$ alkyl, $C_3$-$C_4$ alkenyl; $C_2$-$C_3$ alkyl substituted with $-OCH_3$ or Cl; $C_3$ alkenyl substituted with 1-3 Cl; $C_5$-$C_6$ cycloalkyl; cyclohexenyl; cyclohexyl substituted with 1-3 $-CH_3$; or $-CH_2CH_2OR_7$ where $R_7$ is $-CH_2CH_3$, $-CH(CH_3)_2$, phenyl, $-CH_2CH_2Cl$; or

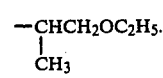

8. A compound of claim 7 where $R_2$ is H, Cl, $CH_3$ or $NO_2$.

9. A compound of claim 7 where $R_2$ is H.

10. A compound of claim 3 where R is $C_1$-$C_4$ alkyl, $C_3$-$C_4$ alkenyl, $C_2$-$C_3$ alkyl substituted with Cl;

or $-CH_2CH_2CH_2O(CH_3$ or $C_2H_5)$.

11. A compound of claim 10 where $R_2$ is H, Cl, $CH_3$ or $NO_2$.

12. A compound of claim 10 where $R_2$ is H.

13. The compound of claim 1, o-methoxycarbonylbenzenesulfonyl isocyanate.

14. The compound of claim 1, o-ethoxycarboylbenzenesulfonyl isocyanate.

15. The compound of claim 1, o-isopropoxycarbonylbenzenesulfonyl isocyanate.

16. The compound of claim 1, o-(2-chloroethoxy)carbonylbenzenesulfonyl isocyanate.

17. The compound of claim 1, o-Allyloxycarbonylbenzenesulfonyl isocyanate.

18. The compound of claim 1, 2-methoxycarbonyl-5-nitrobenzenesulfonyl isocyanate.

19. The compound of claim 1, 2-methoxycarbonyl-5-chlorobenzenesulfonyl isocyanate.

20. The compound of claim 1, 2-isopropoxycarbonyl-5-nitrobenzenesulfonyl isocyanate.

* * * * *